United States Patent [19]

Khokhar et al.

[11] Patent Number: 5,318,962

[45] Date of Patent: Jun. 7, 1994

[54] WATER SOLUBLE 1,2-DIAMINOCYCLOHEXANE PLATINUM (IV) COMPLEXES AS ANTITUMOR AGENTS

[75] Inventors: Abdul R. Khokhar; Zahid H. Siddik; Robert A. Newman, all of Houston, Tex.

[73] Assignee: Board of Regents, The University of Texas System, Austin, Tex.

[21] Appl. No.: 927,201

[22] Filed: Aug. 7, 1992

Related U.S. Application Data

[60] Continuation-in-part of Ser. No. 624,795, Dec. 7, 1990, abandoned, which is a division of Ser. No. 274,824, Nov. 22, 1988, Pat. No. 5,041,578.

[51] Int. Cl.$^5$ .................. C07F 15/00; A61K 31/555
[52] U.S. Cl. .................. 514/184; 514/188; 540/465; 540/541; 548/402; 549/3; 549/206; 549/208; 546/11; 556/137
[58] Field of Search ............... 556/137, 136; 514/188, 514/184, 492; 546/11; 548/403; 549/3, 206, 208; 540/465, 541

[56] References Cited

U.S. PATENT DOCUMENTS

| | | | |
|---|---|---|---|
| 3,904,663 | 9/1975 | Tobe et al. | 260/429 R |
| 4,115,418 | 9/1978 | Gale et al. | 260/429 R |
| 4,137,248 | 1/1979 | Gale et al. | 260/429 R |
| 4,140,707 | 2/1979 | Cleare et al. | 260/429 R |
| 4,169,846 | 10/1979 | Kidani et al. | 260/429 R |
| 4,203,912 | 5/1980 | Hydes et al. | 260/429 R |
| 4,225,529 | 9/1980 | Hydes et al. | 260/429 R |
| 4,230,631 | 10/1980 | Hydes et al. | 260/429 R |
| 4,256,652 | 3/1981 | Kidani et al. | 260/429 R |
| 4,271,085 | 6/1981 | Amundsen et al. | 260/429 R |
| 4,431,666 | 2/1984 | Bulten et al. | 424/287 |
| 4,466,924 | 8/1984 | Verbeek et al. | 260/429 R |
| 4,657,927 | 4/1987 | Cleare et al. | 514/492 |
| 4,661,516 | 4/1987 | Brown et al. | 514/492 |
| 4,680,308 | 7/1987 | Schwartz et al. | 514/492 |
| 4,716,157 | 12/1987 | Bitha et al. | 514/184 |
| 4,760,155 | 7/1988 | Heffernan et al. | 556/136 |
| 4,760,156 | 7/1988 | Heffernan et al. | 556/136 |
| 4,760,157 | 7/1988 | Child et al. | 556/137 |
| 4,845,124 | 7/1989 | Kidani et al. | 514/492 |
| 4,861,905 | 8/1989 | Nowatari et al. | 556/40 |

FOREIGN PATENT DOCUMENTS

| | | |
|---|---|---|
| 569425 | 1/1988 | Australia . |
| 898614 | 5/1984 | Belgium . |
| 0113508 | 7/1984 | European Pat. Off. . |
| 0130482 | 1/1985 | European Pat. Off. . |
| 0136012 | 4/1985 | European Pat. Off. . |
| 0147926 | 7/1985 | European Pat. Off. . |
| 0193936 | 9/1986 | European Pat. Off. . |
| 0237450 | 9/1987 | European Pat. Off. . |
| 2160867A | 1/1986 | United Kingdom . |
| WO87/02364 | 4/1987 | World Int. Prop. O. . |
| WO88/03925 | 6/1988 | World Int. Prop. O. . |

OTHER PUBLICATIONS

Perez-Soler et al., Cancer Research, 47:6462-6466 (Dec. 1987).
Maeda, et al., Japan Journal Cancer Research, 77:523-525 (Jun. 1986).
Vollano et al., J. Med. Chem., 30:716-719 (1987).
Belg. BE 898,614, Chem. Abstracts 101:177510w (1984).

(List continued on next page.)

*Primary Examiner*—Arthur C. Prescott
*Attorney, Agent, or Firm*—Arnold, White & Durkee

[57] ABSTRACT

Water-soluble complexes having the formula:

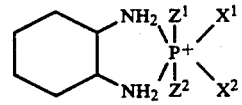

and stereoisomers thereof, where $Z^1$ and $Z^2$ are halogens, and $X^1$ and $X^2$ are selected from the group consisting of sulfate, phosphate, nitrate, and monocarboxylate, or are jointly dicarboxylate, have been found to have desirable antitumor activity, as well as relatively low levels of toxicity.

4 Claims, No Drawings

OTHER PUBLICATIONS

Kihari, Chemical Abstracts 105:134160X (1989).
Craciunescu, Eur. J. Med. Chem., 4:353–357 (1984).
Sur, Oncology, 40:372–376 (1983).
Freise, Archives etc., 258:180–192 (1982).
Kaledin, JNCL, 66:881–886 (1981).
Deliconstantinos, Biochem. Soc. Trans., 5:1326–1328 (1977).
Yatvin, Proc. Am. Assoc. Cancer Res., 21:281 (1980).
Schwartz, Chemical Abstracts, 88:16014K (1978).
Perez-Soler, Cancer Research 46, 6269–6273 (1986).
Connors, Chem. Biol. Interactions, 5:415–424 (1972).
Ridgway, J. Clin. Hematol. Oncol. 7:220–229 (1977).
Burchenal, Chemical Abstracts 93:1125661t (1980).
Appleton, Chemical Abstracts 101:182656c (1984).
Speer, Chemical Abstracts 84:54030n (1976).
Khokhar, Chemical Abstracts 103:226308p (1985).
Tzu, Chemical Abstracts 94:218774t (1981).

WATER SOLUBLE 1,2-DIAMINOCYCLOHEXANE PLATINUM (IV) COMPLEXES AS ANTITUMOR AGENTS

The U.S. government owns certain rights in this invention.

This patent application is a continuation-in-part of U.S. Ser. No. 07/624,795, filed on Dec. 7, 1990, abandoned, which was a divisional of U.S. Ser. No. 07/274,824, filed on Nov. 22, 1988, now issued as U.S. Pat. No. 5,041,578, which is incorporated here by reference.

FIELD OF THE INVENTION

The present invention relates to platinum based drugs and methods of using such drugs and formulations thereof in antitumor therapy.

BACKGROUND OF THE INVENTION

Some platinum based drugs are known to have useful antitumor activity. However, such drugs are also known to have various drawbacks. For example, cisplatin is one such drug with a significant level of activity, but which also exhibits significant nephrotoxicity. Other platinum drugs have been synthesized which have less potential to cause renal injury, but many of these drugs are much less soluble in water than is desirable.

A long standing need exists for platinum drugs which will have improved aqueous solubility and antitumor activity, a broader spectrum of activity against various neoplastic disease states, and also a lack of cross resistance to other antitumor drugs such as cisplatin.

SUMMARY OF THE INVENTION

The present invention includes complexes having the formula

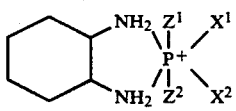

and stereoisomers thereof, where $Z^1$ and $Z^2$ are halogens, preferably chlorine. $X^1$ and $X^2$ are selected from the group consisting of sulfate, phosphate, nitrate, and monocarboxylate, or are jointly dicarboxylate. When $X^1$ and $X^2$ are monocarboxylate, they preferably each have from 1–10 carbon atoms. When $X^1$ and $X^2$ are jointly dicarboxylate, they preferably have between about 2–20 carbon atoms. In one preferred embodiment, $X^1$ and $X^2$ are jointly a dicarboxylate ligand selected from the group consisting of malonate and its derivatives, cycloalkane dicarboxylate, and cycloalkene dicarboxylate.

The present invention also concerns antitumor compositions which include an effective amount of one or more above-described compounds, and a pharmaceutically acceptable carrier. Additionally, the present invention concerns methods of inhibiting neoplastic cell growth, which include the step of administering to a mammal an effective amount of one or more of the above-described complexes.

The complexes, compositions, and methods of the present invention possess significant advantages over the prior art. Platinum (IV) complexes in accordance with the present invention possess high aqueous solubility, high antitumor activity, a broad spectrum of activity, and a lack of cross resistance to other antitumor drugs such as cisplatin. Therefore, the complexes, compositions, and methods of the present invention are believed to have significant therapeutic advantages in the treatment of neoplastic disease states, including the specific cancers of the testes, ovaries, bladder, and head and neck.

DETAILED DESCRIPTION OF SPECIFIC EMBODIMENTS

An example of the synthesis of a complex in accordance with the present invention, (1,1-cyclobutanedicarboxylato) (trans-1,2-diaminocyclohexane) ["DACH"] platinum (IV), is as follows.

The reaction was initiated by the addition of a solution of potassium iodide (28 g, 168 mmol in 50 ml of water) to a filtered aqueous solution of $K_2PtCl_4$ (12 g, 28.9 mmol) in 200 ml of water. Trans-R,R-1,2-diaminocyclohexane (DACH) (3.5 g, 30.7 mmol) in 10 ml of water was added dropwise to the solution of $K_2PtI_4$ and stirring was continued for one hour at room temperature. The brown solid, cis-diiodo-DACH-platinum (II), was removed by filtration and washed successively with $H_2O$, methanol, and ether. After the final product was dried under vacuum, the final yield was 86%.

To prepare the water-soluble sulfato-DACH-platinum, cis-diiodo-DACH-platinum (II) (16.88 g, 0.03 mol) was added to a solution of $Ag_2SO_4$ (8.88 9, 0.0285 mol) in 1800 ml of water. The reaction mixture was stirred overnight at room temperature (protected from light) and the precipitated AgI was removed by filtration. The yellow solution was evaporated to dryness at 45° C. under reduced pressure. A yellow product was obtained which was further purified from water. The yield of sulfato-DACH-platinum was 95%.

DACH-Pt-1,1-cyclobutanedicarboxylate was synthesized by dissolving sulfato-DACH-platinum (0.5447 g) in 20 ml of water and adding to it sodium 1,1-cyclobutanedicarboxylate prepared in situ by the addition of 0.5 ml of 5N NaOH and 0.187 g of 1,1-cyclobutanedicarboxylic acid in 10 ml of water. The reaction mixture was stirred at room temperature for 20 hours, and the white precipitate was separated by filtration and washed with cold water, ethanol, and ether. The final product was recrystallized from water. Hydrogen peroxide (4 ml, 30%) was added to a suspension of DACH-Pt-1,1-cyclobutanedicarboxylate (0.64 g in 100 ml of water). The reaction mixture was left stirring for one hour at 45° C. The clear solution was filtered and the volume of the filtrate was reduced to about 3 ml, and white precipitate was separated by filtration, washed with 3×2 ml of cold water, acetone, ether, and dried under vacuum to give a yield of 91%.

Trans-dichloro(DACH)Pt(IV)-1,1-cyclobutanedicarboxylate was synthesized by adding 125 ml of 0.02N HCl (0.723 mg/ml) to a suspension of DACH-Pt(IV) $(OH)_2$ 1,1-cyclobutanedicarboxylate (0.606 g in 10 ml of water), and leaving the suspension stirring for 30 minutes at room temperature. The light yellow solution was filtered, and the volume of the filtrate was reduced under vacuum to 2 ml. The light yellow product was separated by filtration, washed with 2×2 ml of cold water, and dried under vacuum to give 78% of the final product.

The above procedure can be used to synthesize other complexes in accordance with the present invention.

For example, cyclobutanemonocarboxylic acid or malonic acid can be substituted for 1,1-cyclobutanedicarboxylic acid in this procedure.

Examples of complexes in accordance with the present invention which have been prepared, and their elemental analysis, is shown in Table 1.

TABLE 1

Elemental Analysis of Pt(IV) Complexes

| Complex # | Complex Name | Observed(Calculated) %C | %H | %N |
|---|---|---|---|---|
| 1 | (1,1-cyclobutanedicarboxylato)((trans-R,R-1,2-diaminocyclohexane)trans-dichloroplatinum(IV).2H$_2$O | 25.83(25.80) | 4.42(4.30) | 4.72(5.01) |
| 2 | (1,1-cyclobutanedicarboxylato)(trans-S,S-1,2-diaminocyclohexane)trans-dichloroplatinum(IV).H$_2$O | 26.11(26.66) | 4.66(4.07) | 4.69(5.18) |
| 3 | (1,1-cyclobutanedicarboxylato)(cis-1,2-diaminocyclohexane)trans-dichloroplatinum(IV) | 24.83(25.80) | 4.29(4.30) | 4.69(5.01) |
| 4 | (Trans-R,R-1,2-diaminocyclohexane)trans-dichloro(tartronato)platinum(IV) | 20.73(20.93) | 3.36(3.48) | 5.08(5.42) |
| 5 | (Trans-S,S-1,2-diaminocyclohexane)trans-dichloro(tartronato)platinum(IV) | 21.68(21.68) | 3.65(3.21) | 5.26(5.62) |
| 6 | (Cis-1,2-diaminocyclohexane)trans-dichloro-(tartronato)platinum(IV) | 22.78(21.61) | 3.61(3.21) | 5.18(5.62) |
| 7 | (Trans-R,R-1,2-diaminocyclohexane)trans-dichloro(ketomalonato)platinum(IV) | 21.06(21.01) | 3.50(3.11) | 5.34(5.44) |
| 8 | (Trans-S,S-1,2-diaminocyclohexane)trans-dichloro(ketomalonato)platinum(IV) | 20.90(21.00) | 3.14(3.11) | 5.06(5.44) |
| 9 | (Cis,1,2-diaminocyclohexane)trans-dichloro-(ketomalonato)platinum(IV) | 20.89(21.01) | 3.40(3.11) | 5.48(5.44) |
| 10 | (Trans-R,R-1,2-diaminocyclohexane)trans-dichloro(methylmalonato)platinum(IV) | 20.77(21.81) | 3.82(3.27) | 5.02(5.09) |
| 11 | (Trans-S,S-1,2-diaminocyclohexane)trans-dichloro(methylmalonato)platinum(IV) | 23.42(24.19) | 3.72(3.63) | 5.05(5.64) |
| 12 | (Cis-1,2-diaminocyclohexane)trans-dichloro(methylmalonato)platinum(IV) | 23.28(23.34) | 3.83(3.89) | 4.90(5.44) |

Infrared and NMR spectra for these complexes are given in Table 2 below.

TABLE 2

Infrared and nuclear magnetic resonance spectroscopic data of Pt(IV) complexes

| Complex # | IR$^a$, cm$^{-1}$ $v$(N—H) | $v_{as}$ (C=O) | $v_s$ (C—O) | $v$(M—Cl) | $^{195}$Pt$^b$ $\delta$,ppm |
|---|---|---|---|---|---|
| 1 | 3200br$^c$ | 1630 | 1345 | 340(m)$^d$ | +564 (H$_2$O) |
| 2 | 3200br$^c$ | 1630 | 1346 | 340(m)$^d$ | +580 (H$_2$O) |
| 3 | 3200br$^c$ | 1620 | 1344 | 340(m)$^d$ | |
| 4 | 3190,3074 | 1675 | 1350 | 340(m) | +510 (EtOH) |
| 5 | 3200,3100 | 1658 | 1355 | 340(m) | +514 (EtOH) |
| 6 | 3200,3100 | 1654 | 1349 | 340(m) | +510 (MeOH) |
| 7 | 3190,3074 | 1675 | 1350 | 335(m) | +438 (DMF)$^e$ |
| 8 | 3200,3100 | 1665 | 1350 | 335(m) | +540 (H$_2$O) |
| 9 | 3200,3100 | 1650 | 1369 | 335(m) | |
| 10 | 3170,3070 | 1660 | 1376 | 350(m) | +510 (MeOH) |
| 11 | 3200,3100 | 1623 | 1360 | 350(m) | +490 (H$_2$O) |
| 12 | 3200,3100 | 1626 | 1361 | 350(m) | +509 (MeOH) |

$^a$Infrared spectra are recorded as KBr pellets, and band positions are given in cm$^{-1}$
$^b$$^{195}$Pt chemical shifts are relative to Na$_2$PtCl$_6$ peak at 0.0 ppm
$^c$br: broad band
$^d$m: medium band
$^e$DMF: Dimethylformamide The following examples concern the antitumor activity of the above-identified complexes.

Antitumor Activity Against L1210/0

Cisplatin-sensitive L1210/0 cells (1×10$^5$ cells/mouse) were injected intraperitoneally in male BDF1 mice on day 0, and the drug, in an aqueous medium, was administered intraperitoneally at dose levels ranging from 1.56 to 200 mg/kg on days 1, 5 and 9. The median life spans of control (C) and treated (T) animals were determined, and the percent T/C at the optimal dose calculated as an indicator of antitumor efficacy. Table 3 gives the percent T/C values for each of the 12 complexes, as well as the number of mice cured where applicable.

TABLE 3

Water-soluble DACH-Pt(IV) Complexes.
Antitumor Activity against L1210/0

| Complex | Optimal dose (mg/kg) | % T/C |
|---|---|---|
| 1 | 50 | 471 (2/5) |
| 2 | 100 | 329 (1/5) |
| 3 | 100 | 388 (1/5) |
| 4 | 25 | >600 (3/5) |
| 5 | 50 | 241 |
| 6 | 25 | 218 |
| 7 | 6.25 | >530 (4/5) |
| 8 | 6.25 | 243 |
| 9 | 25 | 205 |
| 10 | 12.5 | >600 (4/5) |
| 11 | 25 | 394 |
| 12 | 50 | 406 (1/5) |

Figures in parentheses indicate number of animals cured/number of animals treated.

Antitumor Activity Against L1210/DDP

Complexes 1–4 and 10 were tested against cisplatin-resistant L1210/DDP cells in an identical manner to that described in above paragraph. The optimal dose, percent T/C and the number cured are given in Table 4.

TABLE 4

Water-soluble DACH-Pt(IV) Complexes.
Antitumor Activity against L1210/DDP

| Complex | Optimal dose (mg/kg) | % T/C |
|---|---|---|
| 1 | 50 | 217 |
| 2 | 50 | 250 (2/5) |
| 3 | 25 | 178 (1/5) |
| 4 | 50 | 214 (1/5) |

TABLE 4-continued

Water-soluble DACH-Pt(IV) Complexes.
Antitumor Activity against L1210/DDP

| Complex | Optimal dose (mg/kg) | % T/C |
|---|---|---|
| 10 | 25 | 195 |

Figures in parentheses indicate number of animals cured/number of animals treated.

Antitumor Activity Against M5076

One million M5076 cells were injected intraperitoneally into BDF1 mice on day 0, and the drugs injected as in the above examples on days 1, 5, 9 and 13. The optimal dose, percent T/C and the number cured for complexes 1-3 are presented in Table 5.

TABLE 5

Water-soluble DACH-Pt(IV) Complexes.
Antitumor Activity against M5076

| Complex | Optimal dose (mg/kg) | % T/C |
|---|---|---|
| 1 | 50 | >415 (5/5) |
| 2 | 25 | >415 (4/5) |
| 3 | 50 | >415 (3/5) |

Figures in parentheses indicate number of animals cured/number of animals treated.

Antitumor Activity Against B16

A 0.5 ml of a 10% B16 brei was injected intraperitoneally on day 0, and complexes 1-3 tested and evaluated in a manner identical to that described for L1210/0 above. The optimal dose and the percent T/C are indicated in Table 6.

TABLE 6

Water-soluble DACH-Pt(IV) Complexes.
Antitumor Activity against B16

| Complex | Optimal dose (mg/kg) | % T/C |
|---|---|---|
| 1 | 50 | 309 |
| 2 | 100 | 283 |
| 3 | 200 | 143 |

The antitumor activity of complexes in accordance with the present invention was compared to that of cisplatin by injecting L1210 murine leukemia cells (100,000) intraperitoneally into BDFI mice on day 0. Six below-listed complexes, as well as cisplatin, were injected intraperitoneally on days 1, 5 and 9 at dose levels ranging from 1.56 mg/kg to 200 mg/kg. Table 7 below gives for each complex the optical dose that appeared from this test, as well as the percent T/C (median survival time of treated mice-median survival time of control mice X 100).

TABLE 7

| Complex | Optimal dose (mg/kg) | % T/C |
|---|---|---|
| Trans-dichloro(1,1-cyclobutanedicarboxylato)(trans-1,2-diaminocyclohexane) platinum (IV) | 50 | 253 |
| Trans-dichloro(1,1-cyclobutanedicarboxylato)(trans-R,R-1,2-diaminocyclohexane) platinum (IV) | 50 | 471 (2/5) |
| Trans-dichloro(1,1-cyclobutanedicarboxylato)(trans-S,S-1,2-diaminocyclohexane) platinum (IV) | 100 | 329 (1/5) |
| Trans-dichloro(1,1-cyclobutanedicarboxylato)(cis-1,2-diaminocyclohexane) platinum (IV) | 100 | 388 (1/5) |
| Trans-dichloro(cyclobutanecarboxylato)(OH)(trans-1,2-diaminocyclohexane) platinum (IV) | 12.5 | 388 (2/5) |
| Trans-dichloro (malonato)(cis,trans-1,2-diaminocyclohexane) platinum (IV) | 50 | 167 |
| Cisplatin | 3 | 218 |

Numbers in parentheses indicates number of animals cured/number of animals treated.

The spectrum of antitumor activity of the complex trans-dichloro (1,1-cyclobutanedicarboxylato) (trans-1,2-diaminocyclohexane) platinum (IV) as compared to that of cisplatin was tested by injecting four different—types of murine tumor cells intraperitoneally into BDF1 mice on day 0. One hundred thousand cells were injected for L1210 and L1210/cisplatin, while 1,000,000 cells were injected for M5076, and 0.5 ml of a 10% brei for B-16. The complex trans-dichloro (1,1-cyclobutanedicarboxylato) (trans-1,2-diaminocyclohexane) platinum (IV) (25 mg/kg) or cisplatin (3 mg/kg) were injected on days 1, 5, and 9 in the case of L1210, L1210/cisplatin, and B-16, and on days 1, 5, 9, and 13 for M5076. The results of this test are shown in Table 8.

TABLE 8

| | % T/C | |
|---|---|---|
| Murine Tumor Model | trans-dichloro (1,1-cyclobutanedicarboxylato)(trans-1,2-diaminocyclohexane) | Cisplatin |
| L1210 | 171 | 218 |
| L1210/cisplatin | 167 | 94 |
| B-16 | 232 | 139 |
| M5076 | 197 (1/5) | 265 |

Numbers in parentheses indicates number of animals cured/number of animals treated.

Compositions in accordance with the present invention can suitably include a pharmaceutically effective amount of one or more platinum complexes in accordance with the present invention, and a pharmaceutically acceptable carrier, such as, for example, water, saline, or dextrose solution. Compositions in accordance with the present invention will contain between about 0.001% and about 99% by weight active complexes, preferably between about 0.001% and about 10%.

Methods in accordance with the present invention comprise administering to a mammal an effective amount of the compounds or complexes described above. The administering step can suitably be parenteral and by intravenous, intraarterial, intramuscular, intralymphatic, intraperitoneal, subcutaneous, intrapleural, or intrathecal injection, or by topical application or oral dosage. Such administration is preferably repeated on a timed schedule until tumor regression or disappearance has been achieved, and may be used in conjunction with other forms of tumor therapy such as surgery or chemotherapy with different agents. The dose administered of a complex in accordance with the present invention can be between about 0.5 and about 50 mg/kg of body weight of the subject to which it is administered.

The description and examples given in this patent are intended to illustrate the present invention. They are not intended to be an exhaustive list of all possible specific embodiments of the present invention. Those skilled in the art will recognize that modifications could be made to the specific embodiments listed here which would still be within the scope of the present invention.

We claim:

1. A complex having the formula

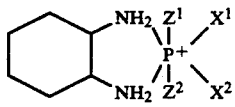

or a stereoisomer thereof, where $Z^1$ and $Z^2$ are halogen, and $X^1$ and $X^2$ are jointly dicarboxylate selected from the group consisting of 1,1-cyclobutanedicarboxylate, methyl malonate, and ketomalonate.

2. The complex of claim 1, wherein $Z^1$ and $Z^2$ are each chlorine.

3. An antitumor composition which includes (a) an amount effective to inhibit neoplastic cell growth of a complex having the formula

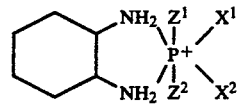

or a stereoisomer thereof, where $Z^1$ and $Z^2$ are halogen, and $X^1$ and $X^2$ are jointly dicarboxylate selected from the group consisting of 1,1-cyclobutanedicarboxylate, methyl malonate, and ketomalonate, and (b) a pharmaceutically acceptable carrier.

4. The composition of claim 3, where $Z^1$ and $Z^2$ are each chlorine.

* * * * *

UNITED STATES PATENT AND TRADEMARK OFFICE
CERTIFICATE OF CORRECTION

PATENT NO. : 5,318,962
DATED : June 7, 1994
INVENTOR(S) : Khokhar, et. al.

It is certified that error appears in the above-indentified patent and that said Letters Patent is hereby corrected as shown below:

On the Title page, item [57], col. 2,

In the chemical formula shown in the abstract; at column 1, line 42; at column 7, line 17; and at column 8, line 11 "P$^+$" should instead be --Pt--.

Signed and Sealed this

Eleventh Day of October, 1994

Attest:

BRUCE LEHMAN

Attesting Officer

Commissioner of Patents and Trademarks